(12) United States Patent
Rostomyan et al.

(10) Patent No.: US 12,241,965 B2
(45) Date of Patent: Mar. 4, 2025

(54) FREQUENCY OFFSET USING SiGe PHASE SHIFTERS

(71) Applicant: BDCM A2 LLC, Dover, DE (US)

(72) Inventors: Narek Rostomyan, San Diego, CA (US); Abdullah Ahsan Zaidi, San Diego, CA (US); Kenneth Ray Carroll, Huntington Beach, CA (US); Maha Achour, Encinitas, CA (US)

(73) Assignee: BDCM A2 LLC, Dover, DE (US)

( * ) Notice: Subject to any disclaimer, the term of this patent is extended or adjusted under 35 U.S.C. 154(b) by 188 days.

(21) Appl. No.: 17/337,318

(22) Filed: Jun. 2, 2021

(65) Prior Publication Data

US 2021/0376464 A1 Dec. 2, 2021

Related U.S. Application Data

(60) Provisional application No. 63/033,497, filed on Jun. 2, 2020.

(51) Int. Cl.
*G01S 13/88* (2006.01)
*A61B 5/11* (2006.01)
*G01S 13/42* (2006.01)

(52) U.S. Cl.
CPC ............. *G01S 13/88* (2013.01); *A61B 5/1114* (2013.01); *G01S 13/426* (2013.01)

(58) Field of Classification Search
CPC ........ G01S 13/88; G01S 13/426; G01S 13/42; G01S 13/751; G01S 7/032; G01S 2013/468; A61B 5/1114; H01Q 21/0025; H01Q 21/065; H01Q 23/00; H01Q 3/22; H01Q 3/36; H01Q 3/42
See application file for complete search history.

(56) References Cited

U.S. PATENT DOCUMENTS

| 7,873,402 B2 * | 1/2011 | Shachar | A61B 1/00158 |
| | | | 600/173 |
| 9,629,561 B2 * | 4/2017 | Weinstein | A61B 5/242 |
| 2010/0130873 A1 * | 5/2010 | Yuen | A61B 5/1126 |
| | | | 600/595 |
| 2010/0231452 A1 * | 9/2010 | Babakhani | H01Q 19/065 |
| | | | 343/753 |

(Continued)

*Primary Examiner* — Olumide Ajibade Akonai
*Assistant Examiner* — Yonghong Li
(74) *Attorney, Agent, or Firm* — Dinsmore & Shohl LLP

(57) ABSTRACT

A radar system for interacting with navigation targets is provided. The radar system is configured to interact with navigation targets (target devices) that shift the phase of a received radar transmission to generate a phase shifted response signal. Phase shifters (e.g., silicon germanium phase shifters) are designed to assign specific frequency responses from one or more navigation modules to identify target locations. The radar module transmits at a modulated signal at first frequency, each navigation target receives the radar transmission, phase shifts the signal and returns the phase shifted signal. Where two or more navigation targets are used, each will apply a different phase shift to the received radar transmission, wherein the frequency identifies the navigation target devices. In a radar system, the modulated transmission signal is compared to the returned phase shifted signal to determine a frequency difference between the two signals.

20 Claims, 9 Drawing Sheets

(56) References Cited

U.S. PATENT DOCUMENTS

2011/0077736 A1* 3/2011 Rofougaran ........ A61M 31/002
                                                      623/8
2016/0218429 A1* 7/2016 Klemes ................... H03K 5/01

* cited by examiner

FREQUENCY OFFSET USING SiGe PHASE SHIFTERS

CROSS-REFERENCE TO RELATED APPLICATIONS

This application claims the benefit of U.S. Provisional Application No. 63/033,497 filed on Jun. 2, 2020, which is incorporated by reference in its entirety for all purposes.

BACKGROUND

As visualization and navigation system capabilities expand there are many new and exciting applications for their use. Particularly in the medical field, cameras and wireless communication provide tools for surgeons and others to gain information that can be used in procedures involving small anatomical regions, giving the physicians additional visualization and accuracy in their work. Robotic applications in medicine is one of many critical applications of new technologies.

BRIEF DESCRIPTION OF THE DRAWINGS

The present application may be more fully appreciated in connection with the following detailed description taken in conjunction with the accompanying drawings, which are not drawn to scale, in which like reference characters refer to like parts throughout, and in which.

DETAILED DESCRIPTION

Figure 1:
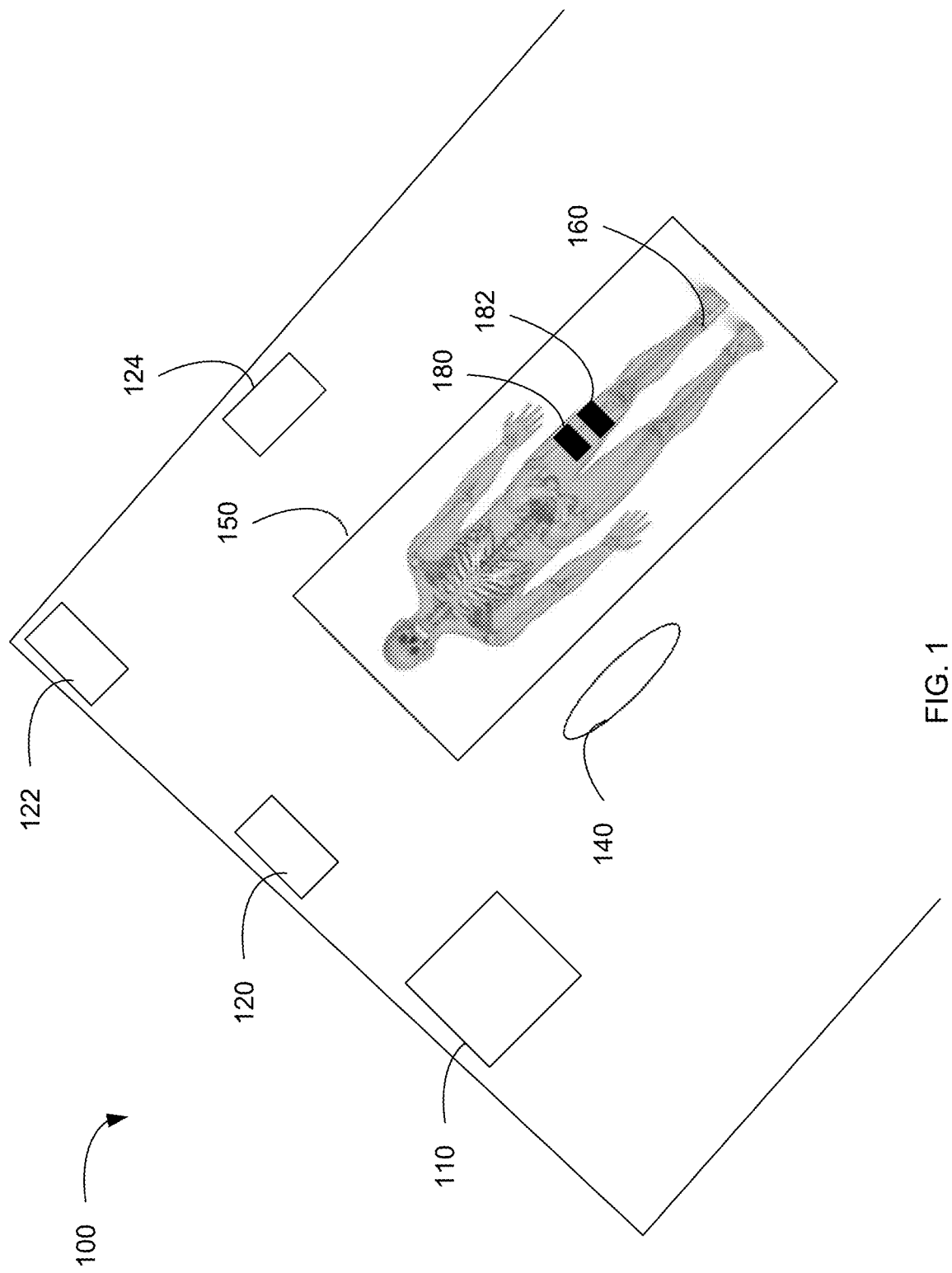
FIG. 1 illustrates an example operating environment incorporating phase shifters, in accordance with one or more implementations of the subject technology.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology is not limited to the specific details set forth herein and may be practiced using one or more implementations. In one or more instances, structures and components are shown in block diagram form in order to avoid obscuring the concepts of the subject technology. In other instances, well-known methods and structures may not be described in detail to avoid unnecessarily obscuring the description of the examples. Also, the examples may be used in combination with each other.

The present invention relates to applications for radar and phase shifter (also referred to herein as "phase shifting") modules in various applications. The present disclosure relates to applications using a radar system for use in the field of medicine. Specifically, the technology disclosed herein relates to a radar system that is configured for use with at least one navigation target device for precise geotagging during a surgery (surgical operation) that requires accuracy and reliability. As used herein, a navigation target device, in different embodiments, can be a silicon germanium (SiGe) based phase shifter and in some implementations comprises radio frequency integrated circuit (RFIC) based phase shifter modules. In some implementations, the navigation target device can include additional passive or active components, e.g., Bluetooth low energy beacons, a general communication device that is configured to receive and transmit signals at 5G, WiFi 6, or any next generation millimeter wave communication protocols. The radar system based on the disclosure may utilize radar and phase shifter modules in various applications. Although specific applications disclosed herein are related to or for medical system, alternate applications may include a wide variety of systems requiring accuracy and reliability.

In the present invention a radar system is configured to interact with navigation modules (navigation target devices) having phase shifters to adjust frequency of received signals. Phase shifters are designed to assign specific frequency responses from one or more navigation modules to identify target locations. The radar module transmits at a modulated signal at first frequency, each navigation target receives the radar transmission, phase shifts the signal and returns the phase shifted signal. Where two or more navigation targets are used, each will apply a different phase shift to the received radar transmission, wherein the frequency identifies the navigation target. In a radar system, the modulated transmission signal is compared to the returned phase shifted signal to determine a frequency difference between the two signals. This is referred to as the Doppler frequency.

In various embodiments, a beamforming or beam steering radar system can be utilized to direct signals from individual antennas over a desired area or Field-of-View (FoV). For radar, this means the area within which the radar can detect objects, or targets. In wireless communications, this means the area within which a user (referred to as having User Equipment (UE)) is detected and a communication is maintained, such as to track a UE. In medical applications, the FoV is limited to an operational area within which procedures are performed. In accordance with various embodiments, the radar system can discern separation distances of individual beacons that are positioned in close proximity, i.e., at a separation distance of or less than, for example, about 1 mm, about 2 mm, about 3 mm, about 5 mm, about 10 mm, about 20 mm, or about 50 mm.

The subject technology is a silicon germanium (SiGe) based multi-channel beamformer (e.g., 4-16 channels) integrated circuit (IC) for transmitter and receiver operations.

The subject technology allows a multitude of applications to achieve accuracy in navigation and identification of targets, even at very small scale, such as for medical applications. The subject technology achieves substantial reduction in area, cost, printed circuit board complexity, and assembly. The subject technology reduces power consumption compared to traditional front-end circuits. The subject technology achieves higher functionality and higher reliability (including higher yield and larger integration capability). The subject technology facilitates integration with digital calibration and serial interfaces, analog and digital converters, various sensors and bias control. The subject technology also lowers packaging parasitic effects and reduces cost with the flip-chip implementation.

In accordance with various embodiments, a navigation target device is provided in detail. The navigation target device is part of an operational (radar) system configured for a medical environment. The navigation can be configured with, among many other components, a receive antenna configured to receive a radar transmission, a transmit antenna configured to transmit a response signal, a phase shifter module coupled between the receive antenna and the transmit antenna, and a controller configured to apply a voltage to the phase shifter module. In some embodiments, the voltage can be a first voltage that corresponds to a first phase shift value, or second or third voltages that corresponds to second or third phase shift values, and so on and so forth. The phase shifter module can be configured to apply the first phase shift value to the radar transmission to generate a response signal. As such, the first phase shift value corresponds to a first frequency that identifies the navigation target device, and similarly, a second frequency can be used to identify a second navigation target device. In some embodiments, the phase shift values are stored in a predetermined lookup table stored within the controller and various components of the radar system. As described herein, the phase shifter module can include a silicon germanium (SiGe) phase shifter and may include additional components, such as a balun, a variable gain antenna, or radio frequency integrated circuits (RFICs). In some implementations, the navigation target device may be implantable and/or encapsulated in a biocompatible shell.

In accordance with various embodiments, a radar system is provided for use in a medical procedure. In some implementations, the radar system may include a radar module adapted to transmit modulated radar signals, at least one navigation target positioned proximate the radar module, and/or a surgical interface in communication with the radar module.

In various implementations, the radar module may include a radar module receive antenna, a radar module transmit antenna, a range-Doppler processor, and/or a radar controller. In some implementations, the navigation target may include a navigation target receive antenna configured to receive radar transmissions from the radar module, a navigation target transmit antenna configured to transmit a response signal, a phase shifter module coupled between the navigation target receive antenna and the navigation target transmit antenna, and/or a navigation target controller adapted to apply a first voltage to the phase shifter module, the first voltage corresponding to a first phase shift value. In some embodiments, the phase shifter module can be configured to apply the phase shift value to the radar transmission to generate the response signal. In some implementations, the surgical interface in communication with the radar module can be configured to provide information comprising a location of at least one navigation target. In some implementations, the radar module can be configured to provide information of the locations of multiple navigation targets. In such cases, the radar module identifies the navigation target by a response signal Doppler frequency of each individual navigation target.

In some implementations, a first navigation target can be configured to apply the first phase shift value to the radar transmission and a second navigation target can be configured to apply a second phase shift value to the radar transmission, and so on and so forth.

In various implementations, the first navigation target and the second navigation target are positioned in a configuration suitable for acquiring locations of the first navigation target and the second navigation target via position triangulation. In some instances, the first phase shift value and the second phase shift value are stored in a predetermined lookup table stored within the navigation target controller. In accordance with various embodiments, one or more navigation targets may be implantable and/or encapsulated in a biocompatible shell.

In accordance with various embodiments, a method of using a navigation target device is disclosed. In various implementations, the method includes receiving, at a receive antenna, a radio frequency (RF) signal at an initial frequency, processing the RF signal from the receive antenna, applying, via a SiGe phase shifter, a voltage value to the RF signal, phase shifting the RF signal to a final frequency based on the applied voltage, and/or transmitting, via a transmit antenna, the phase shifted RF signal at the final frequency. In some implementations, the navigation target device is part of an operational system configured for a medical environment and the phase shifted RF signal that corresponds to the final frequency identifies the navigation target device. In some implementations, the navigation target device is disposed in an anatomical portion of a body for tracking during a medical procedure. In such method, the voltage value is based on a predetermined lookup table stored within the navigation target device. In some implementations, the phase shifting can be performed by a radio frequency integrated circuit based on the predetermined lookup table.

The following passages are described with respect to FIGS. 1-8, and represent non-limiting examples illustrated throughout the present disclosure.

FIG. 1 illustrates an example deployment of a radar system 100 in a medical environment, in accordance with one or more implementations of the subject technology. As illustrated in FIG. 1, the medical environment, such as an operating room or surgical suite, includes a table 150 (e.g., an operating table) where a (patient) body 160 is positioned on the table 150. As shown in the figure, the radar system 100 includes radar modules 120, 122, and 124, a central controller 110 and navigation targets (also referred to herein as "navigation target devices" or "beacons") 180 and 182 to facilitate identification of specific locations on the body 160. The radar modules 120, 122, and 124 are configured to communicate with the navigation targets 180, 182 and are controlled by controller 110. Further details of controller 110 will be described with respect to FIGS. 5 and 6. Each of the navigation targets 180 and 182 is a programmable unit controlled to respond to received radar signals with a specific frequency response. The response is used to identify the location of the corresponding navigation targets 180 and 182. In various embodiments, navigation targets 180 and 182 can be implantable and/or encapsulated in a biocompatible shell. In various embodiments, navigation targets 180 and 182 are consumable navigation targets, e.g., disposable navigation targets. In various embodiments, the navigation targets are self-powered or color-coded. In various embodiments, navigation targets 180 and 182 are pre-programmed for use at a certain frequency. In various embodiments, beacons 180 and 182 are active navigation targets comprising circuitries, such as RFIC, for actively phase shifting, amplifying, etc. The information is presented to a physician via a surgical interface 140. The radar system 100 is configured to provide detailed information to the physician to conduct a surgery or an operation with certainty based on precise locations determined using navigation targets 180 and 182.

In the medical environment illustrated in FIG. 1, the radar system 100 is configured to operate a beam steering radar which may be directed in over a range of angles in azimuth and elevation to detect and identify navigation target devices (also referred to herein as "beacons") 180 and 182, according to various implementations of the subject technology. One or more of the radar modules 120, 122, and 124 may be stationary or may be positioned along a track or other system to position and adjust as desired. Any number of radar modules may be implemented, and in some embodiments, a single unit may be used to cover a specific area. The radar system 100 can scan a Field of View (FoV) or specific area. As described in more detail below, the radar signal is transmitted according to a set of scan parameters that can be adjusted to result in multiple transmission beams. The radar modules 120, 122, and 124 transmit signals modulated according to a Frequency Modulated Continuous Wave (FMCW) as the change in frequency provides information about navigation target devices 180 and 182, with each one implanted or attached to a specific portion of the body 160. An FMCW radar can transmit a sinusoidal signal at linearly increasing frequencies to generate a sawtooth wave when plotted as frequency over time and wherein one cycle is referred to a chirp. Each chirp has a start frequency, a bandwidth and a duration. The slope of the chirp defines the ramp rate of the signal. Other examples may use alternate modulation techniques and may incorporate different waveforms for the transmit signal. The scan parameters of radar modules 120, 122, and 124 may include, among others, the total angle of the scanned area defining the FoV, the beam width or the scan angle of each incremental transmission beam, the number of chirps in the radar signal, the chirp time, the chirp segment time, the chirp slope, and so on. The entire FoV or a portion of it can be scanned by a compilation of such transmission beams, which may be in successive adjacent scan positions or in a specific or random order. Note that the term FoV is used herein in reference to the radar transmissions and does not imply an optical FoV with unobstructed views. The scan parameters may also indicate the time interval between these incremental transmission beams, as well as start and stop angle positions for a full or partial scan.

The radar module 120, 122, and 124 transmits the FMCW signal, Tx; the transmitted signal, Tx, reflects off an object, referred to as a target device (e.g., navigation target devices 180 and 182), and the reflected signal or received signal, Rx, returns to the radar module 120, 122, and 124. Comparison of Tx and the corresponding Rx provides information about the physical distance from the radar modules 120, 122, and 124 to the navigation target devices 180 and 182; this distance is referred to as the range. Various calculations of the signal information can provide more detailed information of navigation target devices 180 and 182. This information may be used to identify the detected object, such as an anatomical portion of a person or vehicle, and parameters associated with the detected object. As the Rx signal is a delayed version of the Tx signal, the Rx signal and the Tx signal are mixed to form an instantaneous frequency (IF) which is the difference in the frequencies of the two signals. Range resolution refers to the ability of the radar module to resolve two closely spaced objects. In a given system if the objects are too close together they will appear as a single peak in the frequency spectrum. To distinguish the objects, the system is designed to increase the length of the IF signal, which increases proportionally with bandwidth. The greater the bandwidth, the greater the resolution will be in a system.

In the present examples, the radar modules 120, 122, and 124 operate to identify the location of the navigational target devices 180, 182. In an example application, the radar modules 120, 122, and 124 each operate at unique frequencies. Consider transmissions, Tx, from radar module 124 at frequency f1. When Tx is received at navigation target device 180, the reflected signal, Rx, returns to radar module 124 from which the target information is determined. In accordance with various embodiments, the navigation target device 180 can include phase shifting circuitry to change the frequency of the Tx signal such that the Rx signal received at the radar module 124 has a frequency shift used to recognize that the signal is returned from navigation target 180 and identify the location of navigation target device 180. Similarly, the navigation target device 182 may include phase shifting circuitry to change the frequency of an incident signal to frequency, f2, which identifies navigation target device 182.

Although not illustrated explicitly in the medical environment of FIG. 1, other components, including for example, perception sensors, such as a camera or a lidar, may be useful in augmenting the object detection capabilities of the radar system 100. A camera or a lidar can be implemented in the radar system 100 to aid the radar modules 120, 122, and 124, and navigation target devices 180 and 182, to detect visible objects and conditions, and to assist in providing auxiliary information to the physician. These may be used to enhance and improve the radar system 100 of FIG. 1. For example, a camera can be used to capture texture, color and contrast information at a high level of detail of a surgery scene in high resolution. A lidar may be used to further enhance the resolution and accuracy of the radar system 100 of FIG. 1.

To further enhance the radar system 100 of FIG. 1, a phase shift to a received signal can provide a change in the Doppler frequency measured and calculated at the one or more radar modules of the radar system 100. The Doppler effect is the apparent change in frequency when a navigation target moves toward or away from the radar transmitter, e.g., radar module 120. The apparent change in the frequency between the source and receiver is due to the relative motion between the source and receiver. This may be used to determine a speed and/or velocity of a detected target by a radar module. In the present system, the change in frequency is introduced by the navigation target, or receiver, as an identifier. For example, the location of the navigation target 180 is thus determined by the range to that navigation target device 180, the angle of arrival of the signal as determined by the radar modules 120, 122, and 124.

Figure 2C:
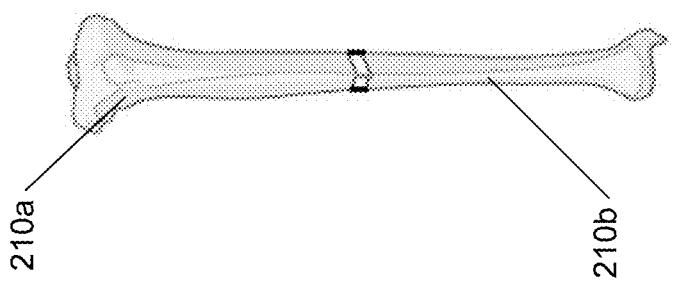
FIGS. 2A-2C illustrate an example anatomical situation wherein a radar system may be implemented in accordance with one or more implementations of the subject technology.
Figure 2B:
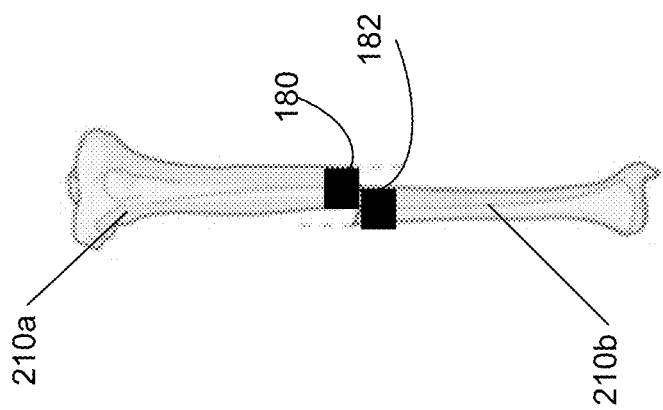
Figure 2A:
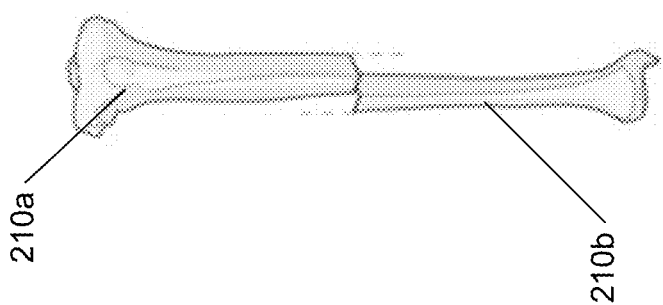

FIGS. 2A-2C illustrate an example anatomical situation wherein a radar system may be implemented in accordance with one or more implementations of the subject technology. As depicted in FIG. 2A, an example of a broken bone is illustrated as two individual pieces—portion 210a and portion 210b. To aid during surgery or operation of the bones, the radar system illustrated in FIG. 1 can be used for aligning or orienting of portion 210a and portion 210b. By using navigation target devices 180 and 182 that are implanted or otherwise disposed at specific locations on the portion 210a and portion 210b of the bone as illustrated in FIG. 2B, the broken bone can be accurately repositioned and realigned using the radar system 100 of FIG. 1. By reading and monitoring locations, positions, angles, etc. of navigation target devices 180 and 182, precise and proper alignment between the portion 210a and portion 210b of the bone can be ensured during the surgery to repair the broken bone. Such monitored information can be made available to a physician via a surgical interface or a computer user interface, which may provide visuals on a monitor, or on smart glasses for physician's use during the procedure, for example, through an augmented or virtual reality system. Once the surgery is completed and the portion 210a and portion 210b of the broken bone are reattached properly, navigation target devices 180 and 182 can be removed as illustrated in FIG. 2C.

Figure 3:
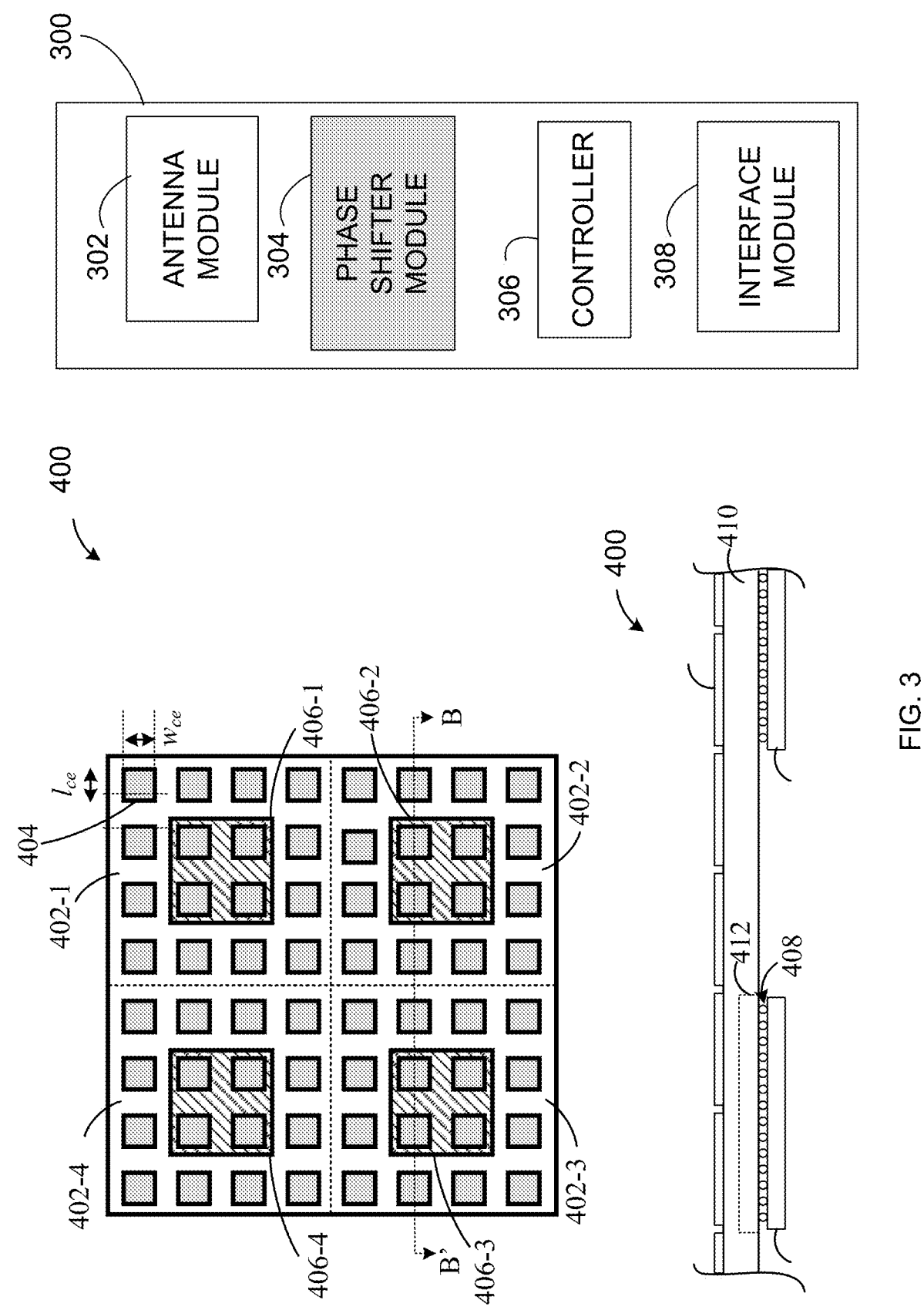
FIG. 3 illustrates a schematic diagram of a phase shifter module (also referred to herein as "phase shifting module") within a navigation target device in accordance with various implementations of the subject technology.

An example of a navigation target device 300 is illustrated in FIG. 3. As shown in FIG. 3, the navigation target device 300 includes a phase shifter module 304 that is configured between an antenna module 302, a controller 306, and an interface module 308. The antenna module 302 has receive and transmit capabilities, which may use a single antenna, separate receive and transmit antennas, and so forth. A receive antenna of the antenna module 302 may be configured to receive a radar transmission or radar signal. A transmit antenna of the antenna module 302 may be configured to transmit a return radar transmission or a response (radar) signal. The phase shifter module 304 may be coupled between the receive antenna and the transmit antenna of the antenna module 302. In operation, the receive antenna receives a radar signal and sends the signal to the phase shifter module 304. The phase shifter module 304 adjusts or phase shifts the frequency in response and transmits the shifted radar signal in a radar transmission to the transmit antenna for transmitting the response signal comprising the phase shifted signal. The interface module 308 allows the navigation target device 300 to interface with other components, such as external devices.

As illustrated in FIG. 3, phase shifter module 304 includes a beamformer integrated tile 400 that is further detailed in a schematic diagram in accordance with one or more implementations of the subject technology. The beamformer integrated circuit package tile 400 includes antenna elements 404 and Radio Frequency Integrated Circuits (RFICs) 406-1, 406-2, 406-3, 406-4. In some implementations, the beamformer integrated circuit package tile 400 includes 64 antenna elements per tile, such that the tile includes a number of channels that corresponds to the number of antenna elements. In some implementations, each tile may be configured as a transmitter (TX) tile or a receiver (RX) tile, where the tile as a transmitter tile includes 64 TX channels or as a receiver tile that includes 64 RX channels. However, the number of antenna elements may be arbitrary and vary depending on implementation. In some implementations, the beamformer integrated circuit package tile 400 includes four (4) 16 channel beamforming ICs (e.g., RFICs 406-1, 406-2, 406-3, 406-4) per tile (based on a 64-element tile), but the number of channels per beamforming IC can vary depending on implementation. The antenna elements 404 may be mounted to a first surface of the beamformer integrated circuit package tile 400 and the RFICs 406-1, 406-2, 406-3, 406-4 may be mounted to a second surface (opposite to the first surface) of the beamformer integrated circuit package tile 400, which will be described in more detail below.

The beamformer integrated circuit package tile 400 may be formed of a specific fabrication technology that allows for high interconnect density, compact routing networks and high frequency applications, such as millimeter wave applications. The beamformer integrated circuit package tile 400 may be an organic packaging-based tile with high precision PCB manufacturing. In some implementations, the beamformer integrated circuit package tile 400 is formed with a Low-Temperature Co-fired Ceramic (LTCC) substrate or package. In other implementations, the beamformer integrated circuit package tile 400 is formed with a Flip-Chip Ball Grid Array (FCBGA) package.

In some implementations, the RFICs 406-1, 406-2, 406-3, 406-4 may include phase shifters for providing RF signals at multiple steering angles. The RFICs 406-1, 406-2, 406-3, 406-4 may include a phase shifting control module for providing phase shifting to transmission lines while mitigating parasitic effects on the transmission lines. As depicted in FIG. 3, the RFICs 406-1, 406-2, 406-3, 406-4 are respectively located in regions 402-1, 402-2, 402-3, 404-4 of the beamformer integrated circuit package tile 400. Each of the regions 402-1, 402-2, 402-3, 404-4 includes a subset of the antenna elements 404, where each corresponding RFIC provides phase shifting to the transmission lines coupled to the corresponding antenna elements in that region. In some examples, the beamformer integrated circuit package tile 400 with a 64-element arrangement can produce horizontal and vertical beam-width of about 12.7 degrees.

In some implementations, each of the antenna elements 404 includes conductive printed elements, such as printed patches of different shapes. In some examples, the antenna elements 404 may be composed of microstrips, gaps, dipoles (e.g., parallel dipoles or cross dipoles), and so forth. The conductive printed elements may also have different configurations, such as a square patch, a rectangular patch, a dipole, multiple dipoles, and so on. Other shapes (e.g., trapezoid, hexagon, etc.) may also be designed to satisfy design criteria for a given millimeter wave application, such as the location of the beamformer integrated circuit package tile 400 relative to the roadway, the desired range and angular resolution performance, and so on. Various configurations, shapes, and dimensions may be used to implement specific designs and meet specific constraints.

As illustrated, beamformer integrated circuit package tile 400 is a rectangular active antenna array with a length l and a width w. For example, the beamformer integrated circuit package tile 400 includes the antenna element 404 that is a rectangular conductive printed patch with dimensions $w_{ce}$ and $l_{ce}$ for its width and length, respectively. The dimensions of the antenna element 404 may be in the sub-wavelength range $$\left(\sim \frac{\lambda}{M}\right),$$

with λ indicating the wavelength of its operational RF signal and M being a positive integer. As described in more detail below, the design of the beamformer integrated circuit package tile 400 is driven by geometrical considerations for a given application. The dimensions, shape and cell configuration of the beamformer integrated circuit package tile 400 will therefore depend on the application.

The cross-sectional view of the beamformer integrated circuit package tile 400 is taken along the B-B' axis. The beamformer integrated circuit package tile 400 includes a substrate 410 with the antenna elements patterned on a top surface of the substrate 410. The RFICs 406-2 and 406-3 are coupled to a bottom surface of the substrate 410 with conductive fasteners 408. In some implementations, the conductive fasteners 408 include solder balls, solder bumps, micro bumps, or the like, for fastening the RFICs 406-2 and 406-3 to the substrate 410 with soldered connections.

In some implementations, the substrate 410 includes a cavity 412 for receiving a RFIC package (e.g., RFIC 406-3) such that the RFIC package is coupled to an inner surface of the cavity 412. In some implementations, the RFIC package can be fastened to the inner surface of the cavity 412 through soldered connections. In other implementations, the cavity may be filled with a resin adhesive to bond the RFIC package to the substrate 410. In this respect, by having the RFIC package inside the cavity 412, the package height of the beamformer integrated circuit package tile 400 is reduced.

Figure 4:
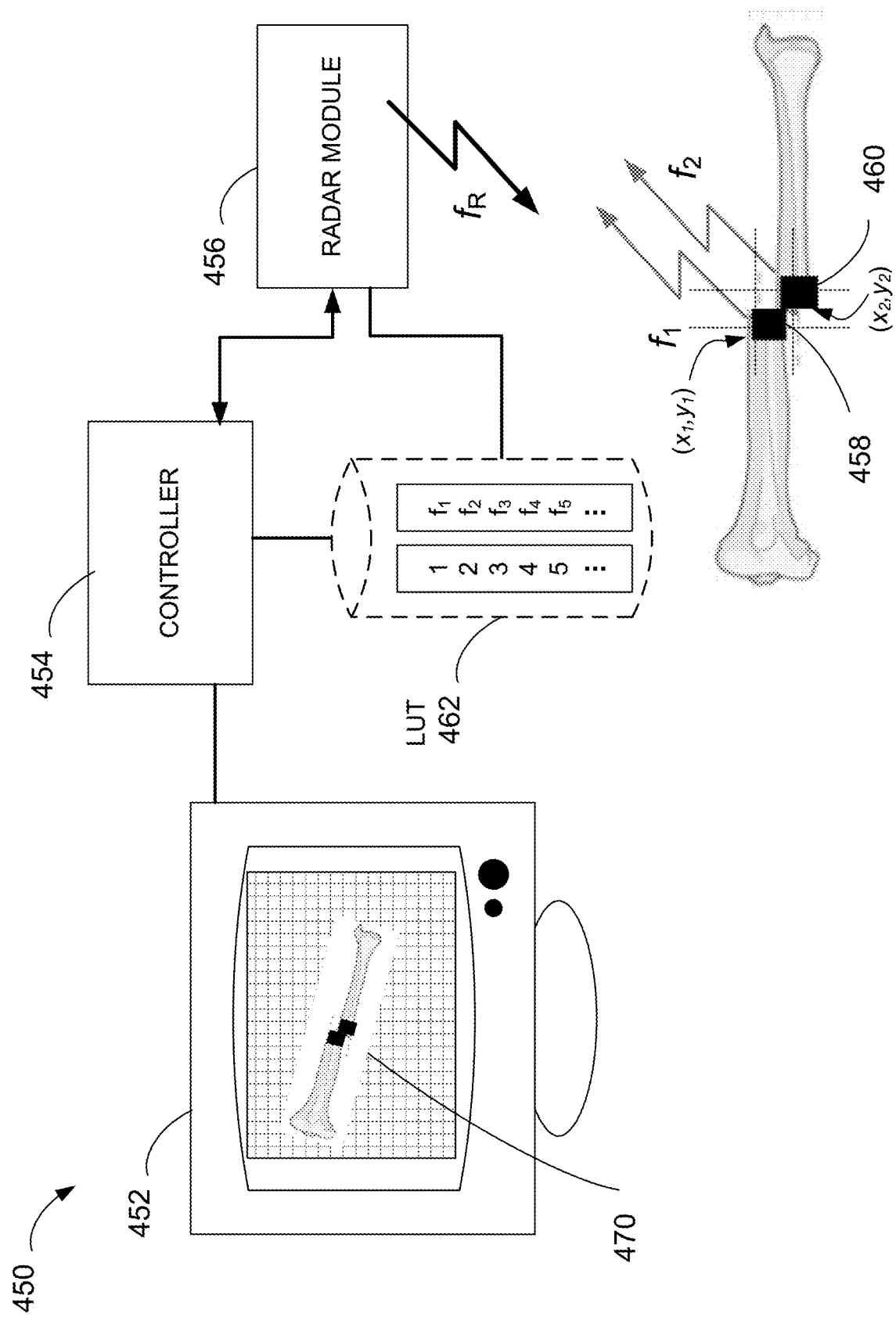
FIG. 4 illustrates a schematic diagram of a radar system in accordance with one or more implementations of the subject technology.

FIG. 4 illustrates a radar system 450 having a radar module 456 and navigation targets 458, 460. A controller 454 controls operation of and receives information from radar module 456. The controller 454 has access to a memory storage, LUT 462, to identify navigation target information and detected information to provide this for visualization on surgical interface 452. The visualization 470 presented to the physician identifies the location of the navigation targets in completing the procedure. The radar system 450 enables the physician to operate on a small scale and with accuracy to improve outcomes. The surgical interface 452 may provide information to other modules, such as robotic instruments and other devices used to accomplish procedures. This information may provide location and alignment to improve alignment, which in the illustrated example is alignment of a broken bone.

Details in the LUT 462 identify each of the navigation targets 458, 460 by response frequency. The radar module 456 receives signals at frequency $f_1$ from navigation target 458 located as position $(x_1,y_1)$ and provides this information to the controller 454. The radar module 456 receives signals at frequency $f_1$ from navigation target 460 located as position $(x_2,y_2)$ and provides this information to the controller 454. While both navigation targets 458, 460 receive signals from radar module 456 at frequency $f_R$, however, each navigation target responds with a different, unique frequency response. The LUT 462 may be positioned with controller 454, distributed among one or more radar modules 456, as a separate module coupled to the system 450 or may be provided as input to the system such as by wireless signaling from a remote computing device.

In operation, the physician, technician or other professional will position navigation target 458 at position $(x_1, y_1)$ and navigation target 458 at position $(x_2, y_2)$. Each navigation target 458, 460 is set, configured, programmed, or so forth to respond to radar signals with a response at a specific frequency that serves to identify the transmitting device, i.e. navigation target. The radar module 456 operates at a given frequency, transmitting FMCW signals, and in response the navigation targets return the received signal at a different frequency, which is achieved through phase shifting within the navigation target. The radar module 456 may generate a range-Doppler (RD) mapping for each received signal, and as the navigation targets 458, 460 each respond with a different frequency, they will be distinguished on the RD mapping. The RD mapping identifies the navigation target and its location. The radar modules 456 may use LUT 462 to identify the navigation target by frequency.

Figure 5:
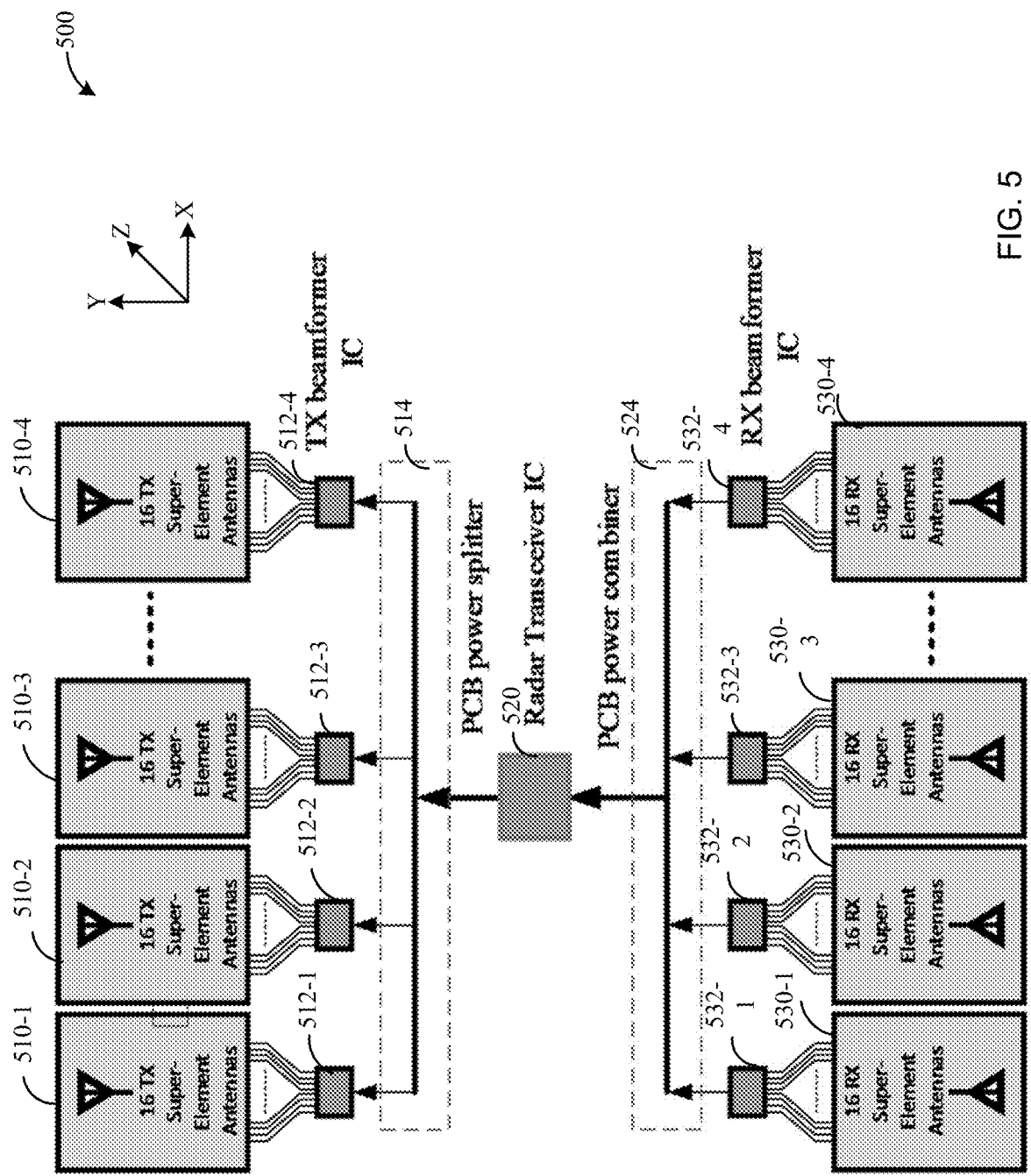
FIG. 5 illustrates a phase shifter module in accordance with one or more implementations of the subject technology.

FIG. 5 illustrates an example of a phase shifter module 500 in accordance with one or more implementations of the subject technology. In various implementations, the phase shifter module 500 is a silicon germanium (SiGe) phase shifter, and in various implementations, comprises one or more variable gain amplifiers (VGAs). FIG. 5 shows a schematic diagram of a 1D radar phased array system 500 in accordance with one or more implementations of the subject technology. The 1D radar phased array system 500 includes transmitter antenna modules 510-1, 510-2, 510-3, and 510-4, transmit beamformer ICs 512-1, 512-2, 512-3 and 512-4, a power splitter 514, a radar transceiver IC 520, a power combiner 524, receiver antenna modules 530-1, 530-2, 530-3, and 530-4, and receive beamformer ICs 532-1, 532-2, 532-3 and 532-4. Not all of the depicted components may be required, however, and one or more implementations may include additional components not shown in the figure. Variations in the arrangement and type of the components may be made without departing from the scope of the claims as set forth herein. Additional components, different components, or fewer components may be provided.

As illustrated in FIG. 5, the transmitter antenna modules 510-1, 510-2, 510-3, and 510-4 are respectively coupled to the transmit beamformer ICs 512-1, 512-2, 512-3 and 512-4 through a multi-channel interface. In some implementations, each of the transmitter antenna modules 510-1, 510-2, 510-3, and 510-4 can include multiple antennas, such as 16 antennas. The transmit beamformer ICs 512-1, 512-2, 512-3 and 512-4 are coupled to the power splitter 514. In some implementations, the power splitter 514 includes a corporate feed network patterned on a Printed Circuit Board (PCB) for distributing a single source input into multiple output signals at respective power levels. The power splitter 514 is coupled to the radar transceiver IC 520. The radar transceiver IC 520 is coupled to the power combiner 524. In some implementations, the power combiner 524 includes a corporate feed network patterned on PCB for combining multiple input signals at respective power levels into a single destination output. The power combiner 524 is coupled to the receive beamformer ICs 532-1, 532-2, 532-3 and 532-4. The receive beamformer ICs 532-1, 532-2, 532-3 and 532-4 are respectively coupled to the receiver antenna modules 530-1, 530-2, 530-3, and 530-4.

In some implementations, each of the transmitter antenna modules 510-1, 510-2, 510-3, and 510-4 includes a substrate (not shown) having multiple conductive layers and a dielectric layer sandwiched therebetween. In various examples, each of the transmitter antenna modules 510-1, 510-2, 510-3, and 510-4 is configured as super elements that are arranged along the x-direction of the 1D radar phased array system 500, in which each super element includes a plurality of slots or discontinuities in the conductive layer proximate antenna elements of the respective transmitter antenna. A signal is provided to each of the super elements that radiates through the slots in the super elements and feeds the antenna elements in the transmitter antenna. The various super elements may be fed with signals of different phase, thus providing phase shifting in the y-direction, while the respective transmitter antenna may be controlled so as to shift the phase of the transmission signal in the y-direction and/or the x-direction, while the signal transmits in the z-direction.

Similar to the transmitter antenna modules 510-1, 510-2, 510-3, and 510-4, each of the receiver antenna modules 530-1, 530-2, 530-3, and 530-4 includes a substrate (not shown) having multiple conductive layers and a dielectric layer sandwiched therebetween. In various examples, each of the receiver antenna modules 530-1, 530-2, 530-3, and 530-4 is configured as super elements that are arranged along the x-direction of the 1D radar phased array system 500, in which each super element includes a plurality of slots or discontinuities in the conductive layer proximate antenna elements of the respective receiver antenna. A signal is received at the antenna elements in the receiver antenna, which is then provided to each of the super elements that radiates through the slots in the super elements and feeds the receive beamformer ICs 532-1, 532-2, 532-3 and 532-4 for phase shifting the incoming RF signaling.

Figure 6:
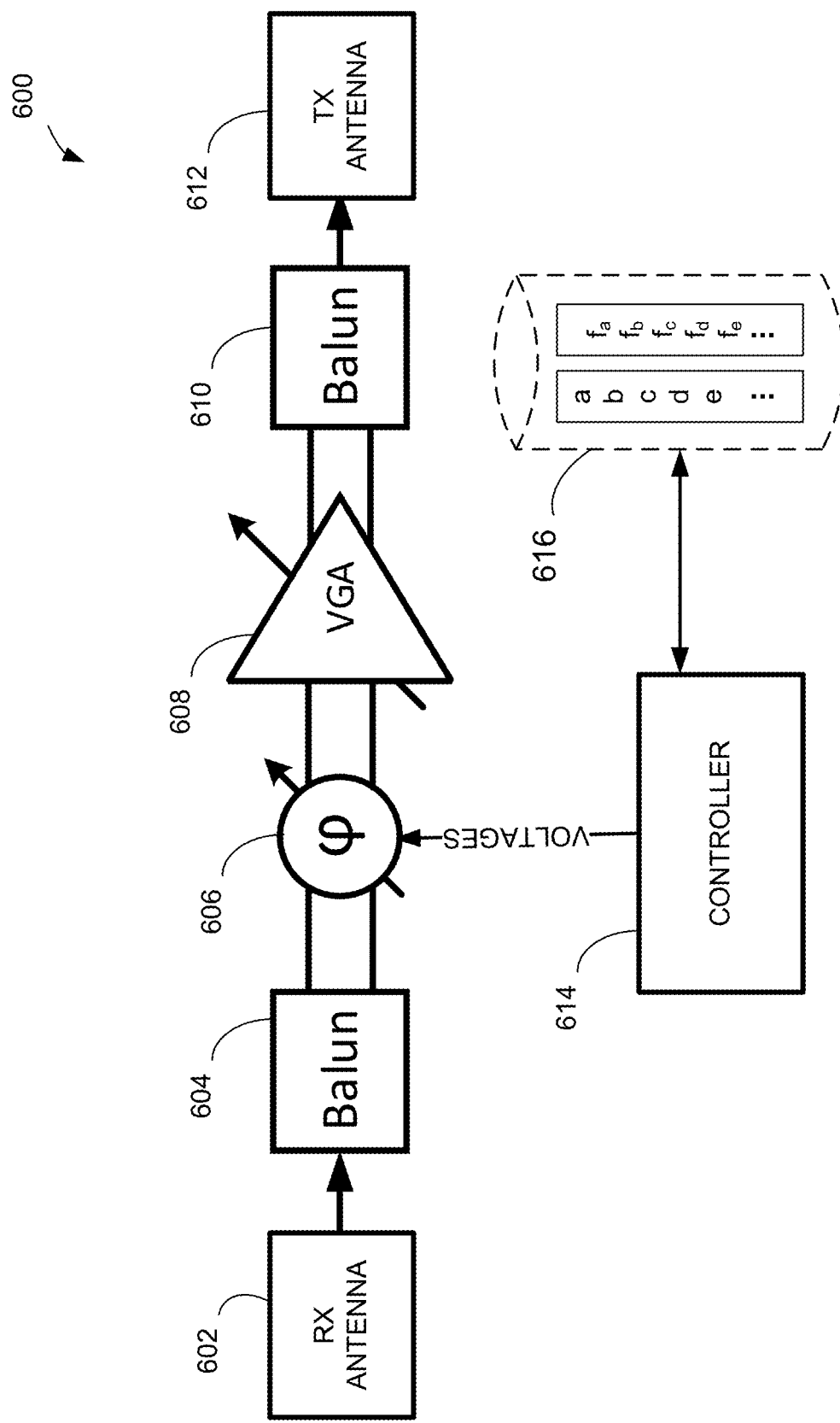
FIG. 6 illustrates a block diagram of a navigation target device in accordance with one or more implementations of the subject technology.

FIG. 6 illustrates a block diagram of a navigation target device 600 in accordance with one or more implementations of the subject technology. As illustrated in FIG. 6, the navigation target device 600 includes a receive antenna 602, a balun 604, a phase shifter module 606, a variable gain amplifier (VGA) 608, a balun 610 and a transmission antenna 612. As implemented, the receive antenna 602 is configured to receive a transmitted signal at an initial or incident frequency. The received signal is then transmitted to a phase shifter module 606 via the balun 604. The phase shifter 606 is a radio frequency integrated circuit (RFIC) that includes a look up table or have access to the controller 614, which has access to look up table (LUT) 616 to identify which frequency to shift to or an amount of required phase shift. In various implementations, the phase shifter module 606 can be a flip chip SiGe phase shifter with VGA chips enabled. The phase shifted signal is then transmitted from the phase shifter 606 to the VGA 608, which is then sent to the transmit antenna 612 via balun 610. The transmit antenna 612 then sends out the phase shifted signal at a different frequency that is different from the initial or incident frequency.

Figure 7:
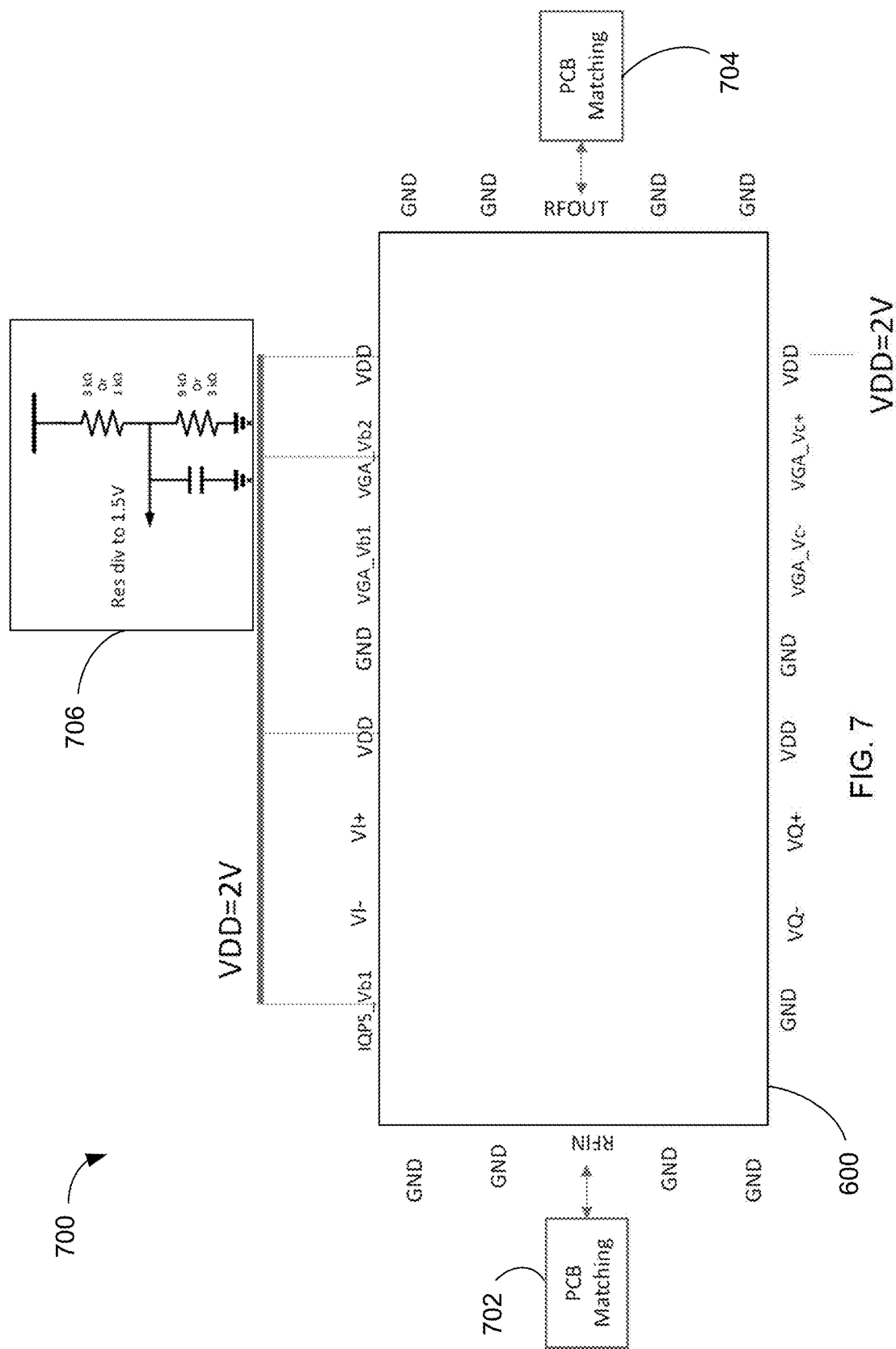
FIG. 7 illustrates a schematic diagram of an example two-dimensional (2D) radar phased array system with beamformer integrated circuit package tiles in accordance with one or more implementations of the subject technology.

FIG. 7 illustrates a schematic diagram of an example radar phased array system 700 with beamformer integrated circuit package tiles in accordance with one or more implementations of the subject technology. As illustrated in FIG. 7, the system 700 includes the phase shift module 600 (shown and described with respect to FIG. 6), a power circuitry 706, two PCB matching circuits 702, 704, and a plurality of ports labeled as indicated in FIG. 7. In some implementations, the system 700 represents a one-channel phase shifter. The phase shifter module 600 is identical or similar to the phase shifter modules 304 or 500 as described with respect to FIGS. 3 and 5, and therefore, will not be described in further detail.

Figure 8:
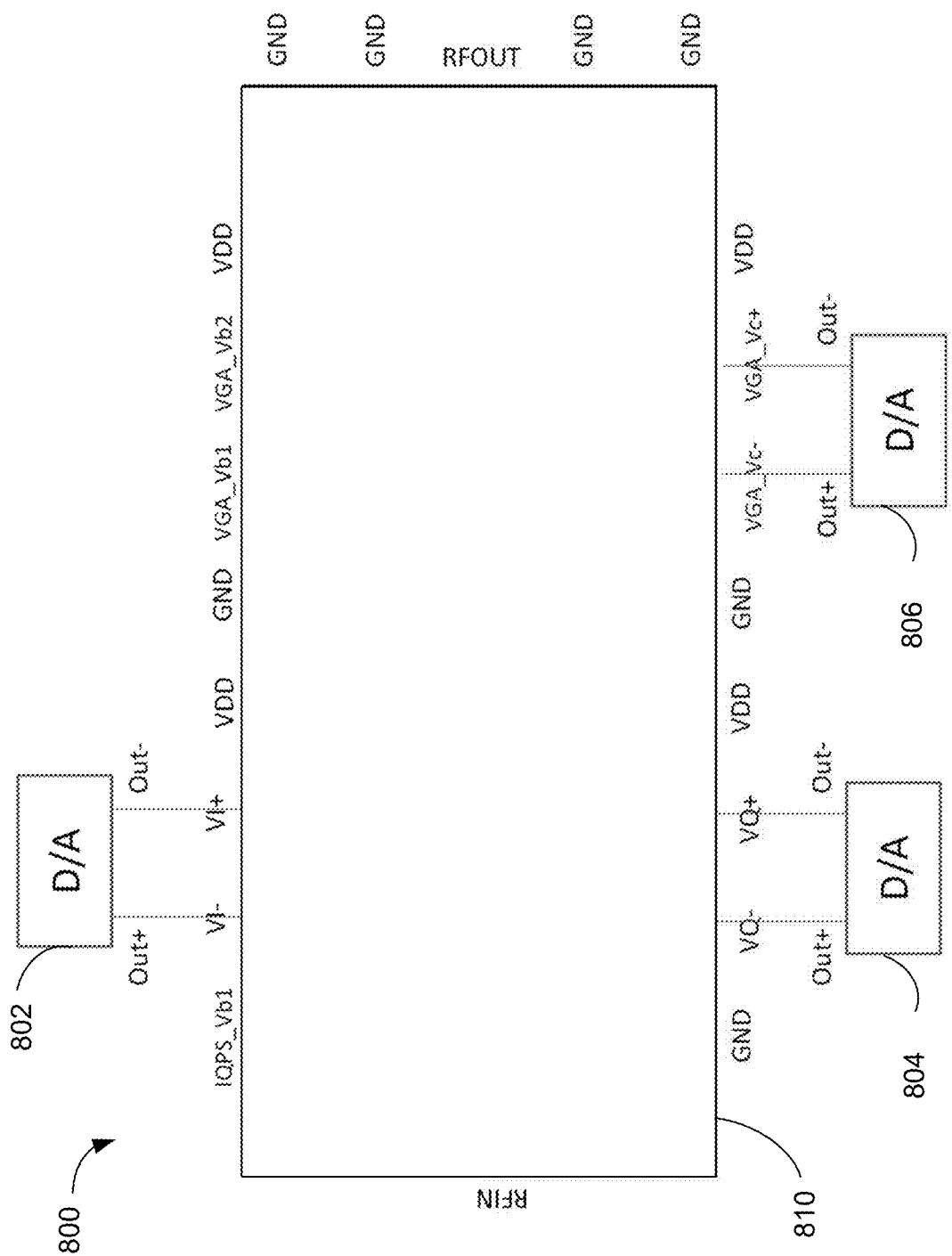
FIG. 8 illustrates a schematic diagram of an example two-dimensional (2D) radar phased array system with beamformer integrated circuit package tiles in accordance with one or more implementations of the subject technology.

FIG. 8 illustrates a schematic diagram of an example two-dimensional (2D) radar phased array system 800 with beamformer integrated circuit package tiles in accordance with one or more implementations of the subject technology. As illustrated in FIG. 8, the system 800 includes a phase shifter module 810 with digital to analog (D/A) modules 802, 804, 806 coupled to voltage ports. The phase shifter module 810 is identical or similar to the phase shifter modules 304, 500, or 600 as described with respect to FIGS. 3, 5, and 6, and therefore, will not be described in further detail. To complete the system 800, an implementation may include supply regulators, low power micro-controller, and other suitable modules.

Figure 9:
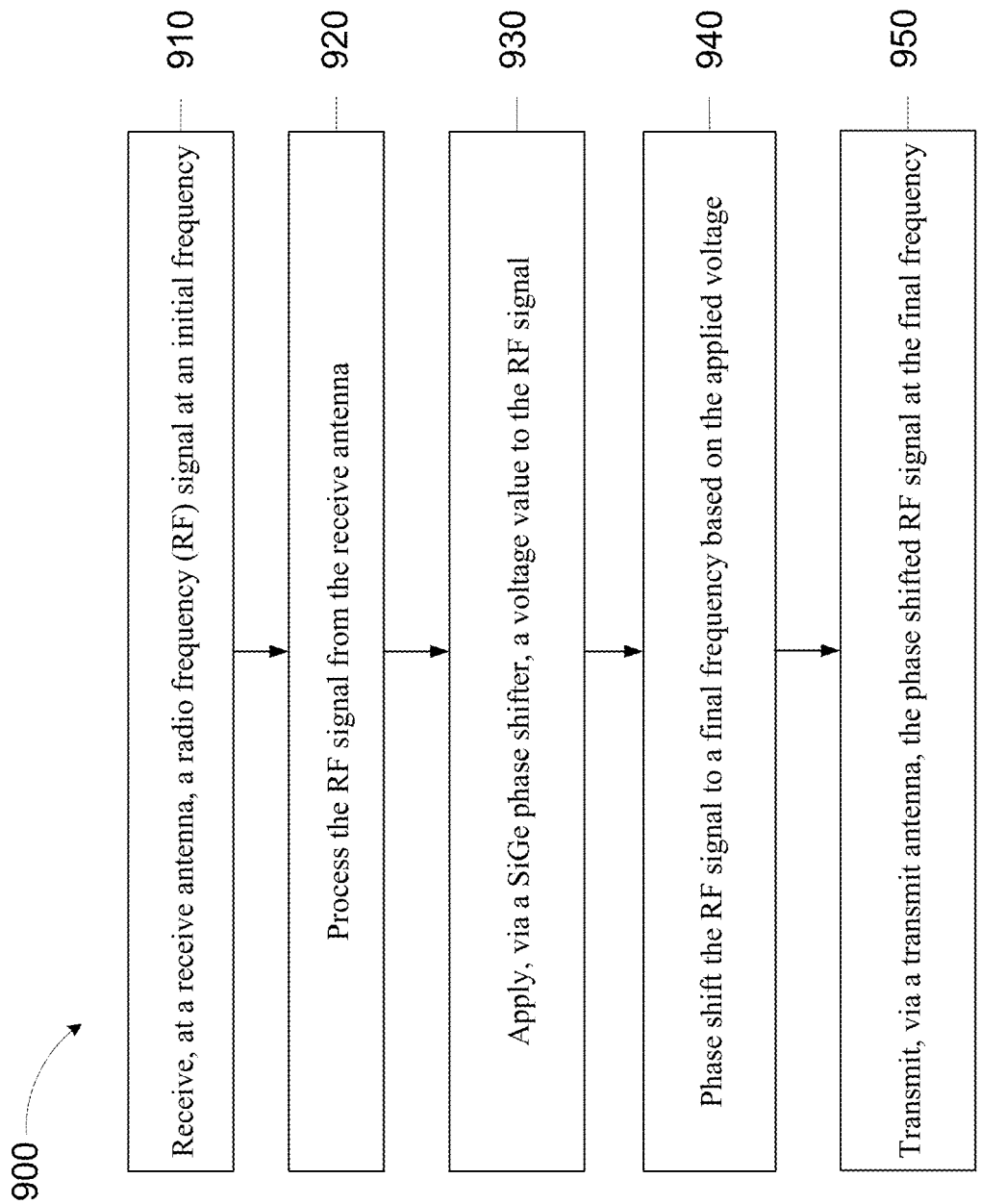
FIG. 9 illustrates a flowchart for an example method of using a radar system in accordance with one or more implementations of the subject technology.

FIG. 9 illustrates a flowchart for a method 900 of using a radar system, in accordance with one or more implementations of the subject technology. The method 900 includes, at step 910, receiving, at a receive antenna, a radio frequency (RF) signal at an initial frequency. Using a radar system, such as the radar system 100 of FIG. 1 (or radar system 300 of FIG. 3), the RF signal can be transmitted from any of the radar modules 120, 122, or 124. The method 900 includes, at step 920, processing the RF signal from the receive antenna. The processing of the RF signal can be performed at the phase shifter module, as disclosed herein. The method 900 also includes at step 930, applying, via a phase shifter module (e.g., the phase shifter modules 304, 500, 600, or SiGe phase shifter), a voltage value to the RF signal. The method 900 includes, at step 940, phase shifting the RF signal to a final frequency based on the applied voltage. The method 900 includes, at step 950, transmitting, via a transmit antenna, the phase shifted RF signal at the final frequency. In some implementations, the voltage value is based on a predetermined lookup table stored within the navigation target device. In some implementations, the phase shifting is performed by a radio frequency integrated circuit (RFIC) based on the predetermined lookup table. In some implementations, the navigation target device is part of an operational system configured for a medical environment and the phase shifted RF signal that corresponds to the final frequency identifies the navigation target device. In some implementations, the navigation target device is disposed in an anatomical portion of a body for tracking during a medical procedure In accordance with various embodiments and implementations, a navigation target device is provided. The navigation target device includes a receive antenna configured to receive a radar transmission; a transmit antenna configured to transmit a response signal; a phase shifter module coupled between the receive antenna and the transmit antenna; and a controller configured to apply a first voltage to the phase shifter module, the first voltage corresponding to a first phase shift value, wherein the phase shifter module applies the first phase shift value to the radar transmission to generate the response signal.

In some implementations, the first phase shift value corresponds to a first frequency that identifies the navigation target device. In some implementations, the phase shifter module comprises a silicon germanium (SiGe) phase shifter. In some implementations, the navigation target device is part of an operational system configured for a medical environment. In some implementations, the first phase shift value is based on a predetermined lookup table stored within the controller.

In some implementations, the navigation target device further includes a balun and a variable gain antenna. In some implementations, the navigation target device further includes one or more radio frequency integrated circuits (RFICs). In some implementations, the navigation target device is implantable and is encapsulated in a biocompatible shell.

In various implementations, a radar system is provided. The radar system includes a radar module adapted to transmit modulated radar signals, the radar module comprising: a radar module receive antenna, a radar module transmit antenna, a range-Doppler processor, and a radar controller. The radar system includes at least one navigation target positioned proximate the radar module, comprising: a navigation target receive antenna configured to receive radar transmissions from the radar module, a navigation target transmit antenna configured to transmit a response signal, a phase shifter module coupled between the navigation target receive antenna and the navigation target transmit antenna, and a navigation target controller adapted to apply a first voltage to the phase shifter module, the first voltage corresponding to a first phase shift value, wherein the phase shifter module applies the phase shift value to the radar transmission to generate the response signal. The radar system includes a surgical interface in communication with the radar module configured to provide information comprising a location of the at least one navigation target.

In some implementations, the radar module identifies the at least one navigation target by a response signal Doppler frequency. In some implementations, the radar system is used for a medical procedure. In some implementations, the at least one navigation target comprises a first navigation target that applies the first phase shift value to the radar transmission and a second navigation target that applies a second phase shift value to the radar transmission. In some implementations, the first navigation target and the second navigation target are positioned in a configuration for acquiring locations of the first navigation target and the second navigation target via position triangulation. In some implementations, the first phase shift value and the second phase shift value are stored in a predetermined lookup table stored within the navigation target controller. In some implementations, the at least one navigation target is implantable and is encapsulated in a biocompatible shell.

In various implementations, a method of using a navigation target device is provided. The method includes receiving, at a receive antenna, a radio frequency (RF) signal at an initial frequency; processing (e.g., at a phase shifter module) the RF signal from the receive antenna; applying, via a SiGe phase shifter, a voltage value to the RF signal; phase shifting the RF signal to a final frequency based on the applied voltage; and transmitting, via a transmit antenna, the phase shifted RF signal at the final frequency.

In some implementations, the voltage value is based on a predetermined lookup table stored within the navigation target device. In some implementations, the phase shifting is performed by a radio frequency integrated circuit (RFIC) based on the predetermined lookup table. In some implementations, the navigation target device is part of an operational system configured for a medical environment and the phase shifted RF signal that corresponds to the final frequency identifies the navigation target device. In some implementations, the navigation target device is disposed in an anatomical portion of a body for tracking during a medical procedure.

It is appreciated that the previous description of the disclosed examples is provided to enable any person skilled in the art to make or use the present disclosure. Various modifications to these examples will be readily apparent to those skilled in the art, and the generic principles defined herein may be applied to other examples without departing from the spirit or scope of the disclosure. Thus, the present disclosure is not intended to be limited to the examples shown herein but is to be accorded the widest scope consistent with the principles and novel features disclosed herein.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim.

A reference to an element in the singular is not intended to mean "one and only one" unless specifically stated, but rather "one or more." The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While this specification contains many specifics, these should not be construed as limitations on the scope of what may be claimed, but rather as descriptions of particular implementations of the subject matter. Certain features that are described in this specification in the context of separate implementations can also be implemented in combination in a single implementation. Conversely, various features that are described in the context of a single implementation can also be implemented in multiple implementations separately or in any suitable sub combination. Moreover, although features may be described above as acting in certain combinations and even initially claimed as such, one or more features from a claimed combination can in some cases be excised from the combination, and the claimed combination may be directed to a sub combination or variation of a sub combination.

The subject matter of this specification has been described in terms of particular implementations, but other aspects can be implemented and are within the scope of the following claims. For example, while operations are depicted in the drawings in a particular order, this should not be understood as requiring that such operations be performed in the particular order shown or in sequential order, or that all illustrated operations be performed, to achieve desirable results. The actions recited in the claims can be performed in a different order and still achieve desirable results. As one example, the processes depicted in the accompanying figures do not necessarily require the particular order shown, or sequential order, to achieve desirable results. Moreover, the separation of various system components in the aspects described above should not be understood as requiring such separation in all implementations, and it should be understood that the described program components and systems can generally be integrated together in a single hardware product or packaged into multiple hardware products. Other variations are within the scope of the following claim.

What is claimed is:

1. A navigation target device for medical application, comprising:
   a receive antenna configured to receive a radar transmission from a radar system, the radar transmission from an anatomical portion of a person and configured to align different locations;
   a transmit antenna configured to transmit a response signal based on the received radar transmission;
   a phase shifter module coupled between the receive antenna and the transmit antenna and adapted to identify the different locations; and
   a controller configured to apply a first voltage of a plurality of voltages to the phase shifter module, the first voltage corresponding to a first phase shift value, and the first phase shift value enables identification of the navigation target device from one or more other navigation target devices and to identify the location of the anatomical portion of the person associated with the navigation target device, wherein the phase shifter module is configured to apply the first phase shift value to the received radar transmission and generate the response signal corresponding to identification of the navigation target device from the one or more other navigation target devices, and wherein the navigation target device is encapsulated in a biocompatible shell.

2. The navigation target device of claim 1, wherein the first phase shift value corresponds to a first frequency that identifies the navigation target device.

3. The navigation target device of claim 1, wherein the phase shifter module comprises a silicon germanium (SiGe) phase shifter.

4. The navigation target device of claim 1, wherein the navigation target device is part of an operational system that is configured to work with the radar system for a medical environment.

5. The navigation target device of claim 1, wherein the first phase shift value is based on a predetermined lookup table stored within the controller.

6. The navigation target device of claim 1, further comprising a balun and a variable gain antenna.

7. The navigation target device of claim 1, further comprising one or more radio frequency integrated circuits (RFICs).

8. The navigation target device of claim 1, wherein the navigation target device is implantable.

9. A radar system, comprising:
a radar module adapted to transmit modulated radar signals, the radar module comprising:
  a radar module receive antenna configured to receive signals from an anatomical portion of a person and configured to align different locations,
  a radar module transmit antenna,
  a range-Doppler processor, and
  a radar controller;
at least one navigation target positioned proximate the radar module, comprising:
  a navigation target receive antenna configured to receive a radar transmission from the radar module,
  a navigation target transmit antenna configured to transmit a response signal based on the received radar transmission,
  a phase shifter module coupled between the navigation target receive antenna and the navigation target transmit antenna, and
  a navigation target controller adapted to apply a first voltage of a plurality of voltages to the phase shifter module, the first voltage corresponding to a first phase shift value, and the first phase shift value enables identification of the at least one navigation target from one or more other navigation targets and to identify the location of the anatomical portion of the person associated with the at least one navigation target,
    wherein the phase shifter module is adapted to apply the phase shift value to the received radar transmission and generate the response signal corresponding to identification of the at least one navigation target from the one or more other navigation targets; and
a surgical interface in communication with the radar module configured to provide information comprising a location of the at least one navigation target.

10. The radar system of claim 9, wherein the radar module identifies the at least one navigation target by a response signal Doppler frequency.

11. The radar system of claim 9, wherein the radar system is used for a medical procedure.

12. The radar system of claim 9, wherein the at least one navigation target comprises a first navigation target that applies the first phase shift value to the received radar transmission and a second navigation target that applies a second phase shift value to the received radar transmission.

13. The radar system of claim 12, wherein the first navigation target and the second navigation target are positioned in a configuration for acquiring locations of the first navigation target and the second navigation target via a geometric position triangulation.

14. The radar system of claim 12, wherein the first phase shift value and the second phase shift value are stored in a predetermined lookup table stored within the navigation target controller.

15. The radar system of claim 9, wherein the at least one navigation target is implantable and is encapsulated in a biocompatible shell.

16. A method of using a navigation target device, comprising:
receiving, at a receive antenna configured to align different anatomical portions of a person or a vehicle, a radio frequency (RF) signal from a radar system;
processing the RF signal from the receive antenna;
applying, via a SiGe phase shifter, a voltage value of a plurality of voltage values to the RF signal thereby phase shifting the RF signal by a first phase shift value corresponding to the voltage value, wherein the first phase shift value enables identification of the navigation target device from one or more other navigation target devices and to identify the location of the anatomical portion of the person associated with the navigation target device; and
transmitting, via a transmit antenna, the phase shifted RF signal, wherein the phase shifted RF signal corresponds to identification of the navigation target device from the one or more other navigation target devices,
wherein the navigation target device is encapsulated in a biocompatible shell.

17. The method of claim 16, wherein the voltage value is based on a predetermined lookup table stored within the navigation target device.

18. The method of claim 16, wherein the phase shifting is performed by a radio frequency integrated circuit (RFIC) based on a predetermined lookup table.

19. The method of claim 16, wherein the navigation target device is part of an operational system that is configured to work with the radar system for a medical environment and the phase shifted RF signal identifies the navigation target device.

20. The method of claim 16, wherein the navigation target device is disposed in an anatomical portion of a body for tracking during a medical procedure.

* * * * *